United States Patent [19]

Klemm et al.

[11] 4,051,242

[45] Sept. 27, 1977

[54] SUBSTITUTED N-ACYL-N''-(3-AMINO-2-CYANOACRYL-OYL-)FORMAMIDRAZONES

[75] Inventors: Kurt Klemm, Allensbach, Germany; Erhard Langenscheid, late of Constance, Germany

[73] Assignee: Byk Gulden Lomberg Chemische Fabrik GmbH, Constance, Germany

[21] Appl. No.: 499,522

[22] Filed: Aug. 22, 1974

[30] Foreign Application Priority Data

Aug. 27, 1973 Luxembourg .......................... 68317

[51] Int. Cl.² .......................................... C07D 295/00

[52] U.S. Cl. .................................... 424/246; 544/163; 544/58; 260/268 PH; 260/268 CN; 260/293.85; 260/293.86; 260/293.87; 260/294.8 E; 260/326.43; 260/465 D; 424/248.55; 424/267; 424/274; 424/300; 424/304; 424/248.54

[58] Field of Search ................ 260/247.2 A, 268 PH, 260/268 CN, 465 D, 293.85, 293.86, 293.87, 326.43, 243 B; 424/246, 248, 267, 274, 300, 304

[56] References Cited

U.S. PATENT DOCUMENTS 3,923,817  12/1975  Klemm ........................... 260/293.87

*Primary Examiner*—Paul J. Killos
*Attorney, Agent, or Firm*—Berman, Aisenberg & Platt

[57] ABSTRACT

Therapeutically-active and pharmacologically-acceptable N-acyl-N''-(3-amino-2-cyanoacryloyl)-formamidrazones and their pharmaceutically-acceptable acid-addition salts inhibit xanthine oxidase and are useful as the active ingredient in medicaments for the treatment of gout.

27 Claims, No Drawings

SUBSTITUTED N-ACYL-N''-(3-AMINO-2-CYANOACRYLOYL-)FORMAMIDRAZONES

The invention relates to therapeutically-valuable substituted N-acyl-N''-(3-amino-2-cyanoacryloyl)-formamidrazones having, more particularly, xanthine-oxidase inhibiting properties.

Derivatives of pyrazolo[3,4-d] pyrimidines have been known for a long time which have enzyme-inhibiting properties. Thus for example 4-hydroxy-1H-pyrazolo[3,4-d] pyrimidine, which is known under the name "Allopurinol" inhibits the enzyme, xanthine oxidase.

This enzyme catalyses in vivo oxidation of purine derivatives to produce uric acid. In the same manner allopurinol suppresses the oxidation of 6-mercaptopurine to 6-thiouric acid [German patent specification (Offenlegungsschrift) 1,904,894).

Since Allopurinol strongly reduces the quantities of uric acid produced in purine metabolism, it is used therapeutically for the treatment of gout. A disadvantage of allopurinol is, however, that it has a relatively high acute toxicity and is employed in doses, which are relatively high taking into account its toxicity, between 100 and 800 mg per person and per day. It was therefore desirable to develop products which, while having a substantially lower toxicity, also inhibit xanthine oxidase and can be used for the treatment of gout.

The subject matter of the present invention includes substituted N-acyl-N''-(3-amino-2-cyanoacryloyl)formamidrazones of the general formula I

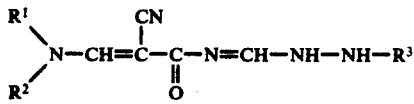

and their tautomers and salts with organic and inorganic acids, in which $R^1$ and $R^2$ are the same or different and denote a hydrogen atom, a straight chained or branch chained alkyl radical with 1 to 7, preferably 1 to 4 carbon atoms, or a cycloalkyl radical with 3 to 6 carbon atoms, in the case of which if one of the radicals $R^1$ or $R^2$ denotes a hydrogen atom, the other radical has a meaning differing from hydrogen, or in which $R^1$ and $R^2$ together denote an alkylene group with 2 to 5 carbon atoms, in which possibly one or more methylene groups can be replaced by a hetero atom, for example —O— and —S—, or by the —$NR^7$ group, for example a 3-aza-, 3-thia-, 3-oxa-pentamethylene group or a pentamethylene group, $R^3$ denotes one of the following radicals

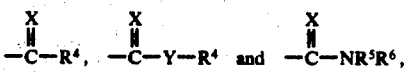

in which $R^4$ denotes a hydrogen atom, a straight chained or branch chained alkyl radical with 1 to 14 carbon atoms, in which possibly a methylene (other than a-methylene) group can be replaced by an oxygen atom (e.g. an alkyl radical wherein a carbon chain is optionally interrupted by an oxygen atom), a cycloalkyl radical with 3 to 6 carbon atoms, a phenyl radical substituted by straight chained or branch chained alkyl, alkoxy or alkylmercapto groups with 1 to 7, preferably 1 to 4 carbon atoms, alkoxycarbonyl groups with 2 to 5 carbon atoms, halogen, trifluoromethyl, nitro and/or cyano groups or preferably unsubstituted, or a phenyl-alkyl radical in the case of which the alkyl radical is straight chained or branch chained and possesses 1 to 6, preferably 1 or 2 carbon atoms, in the case of which the phenyl radical optionally is substituted as above, and in which the alkyl or cycloalkyl radicals may be substituted by a salt-forming basic group, more particularly a —$NR^5R^6$ group, $R^5$ and $R^6$ are the same or different and denote a hydrogen atom, a straight chained or branch chained alkyl radical with 1 to 7, preferably 1 to 4 carbon atoms, in which possibly a methylene group can be replaced by an oxygen atom, or a cycloalkyl radical with 3 to 6 carbon atoms or $R^5$ and $R^6$ together denote an alkylene group with 2 to 5 carbon atoms, in which possibly one or more methylene groups can be replaced by a hetero atom as for example —O—, —S— or by the —$NR^7$— group, as for example a 3-aza or 3-thia—, preferably a 3-oxa-pentamethylene group and more particularly a pentamethylene group, X denotes a sulfur atom or an —$NR^7$— group, more particularly an oxygen atom, Y denotes a sulfur atom or more particularly an oxygen atom, and $R^7$ denotes a hydrogen atom, a straight chained or branch chained alkyl radical with 1 to 7, more particularly 1 to 5 carbon atoms, possibly substituted by a hydroxy group, or a phenyl radical, possibly substituted by a straight chained or branch chained alkyl- or alkoxy radical with 1 to 7, more particularly 1 to 4 carbon atoms, halogen or trifluoromethyl.

A straight chained or branch chained alkyl group with up to 7 carbon atoms is for example a methyl, ethyl, propyl, isopropyl, butyl, isobutyl, sec.-butyl or tert.-butyl, pentyl, isopentyl, 1- or 2-methyl-butyl, tert.-pentyl, hexyl, isohexyl, 1-, 2- or 3-methyl-pentyl, 1-, 2- or 3-ethyl-butyl, 1,2-, 1,3- or 2,3-dimethyl-butyl, heptyl or isoheptyl group. It can, however, also be unsaturated and is then for example a vinyl, allyl, 2-methyl-allyl, propene-1-yl, butene-1- or 2-yl, 2-methyl-propene-1-yl, propyn-1- or 2-yl, pentene-1, 2, 3 or 4-yl, hexene-1, 2, 3, 4 or 5-yl, heptene-1, 2, 3, 4, 5 or 6-yl or pentadiene-1,4-, 1,3-, or 2,4-yl group.

A straight chained or branch chained alkoxy or alkylmercapto group with 1 to 7 carbon atoms is for example an alkoxy group, derived from the above-mentioned alkyl groups with up to 7 carbon atoms, the alkoxy group being for example a methoxy, ethoxy, propoxy, isopropoxy, butoxy, isobutoxy, sec.-butoxy or tert.-butoxy group or an alkylmercapto group, derived from the above, as for example a methylmercapto, ethylmercapto, propylmercapto, isopropylmercapto or butylmercapto group.

A cycloalkyl group with 3 to 6 carbon atoms is for example a cyclopropyl, cyclopentyl, 2- or 3-methyl-cyclopentyl or preferably a cyclohexyl group.

An alkylene group derived from the radicals $R^1$ and $R^2$ and, respectively $R^5$ and $R^6$ with 2 to 5 carbon atoms is straight chained or branch chained and is for example an ethylene, trimethylene, 1- or 2-methyl-ethylene, tetramethylene, 1-, 2- or 3-methyl-trimethylene, 1- or 2-ethyl-ethylene or pentamethylene group.

A halogen atom is a fluorine or iodine atom and more particularly a chlorine or bromine atom.

An alkoxycarbonyl group with 2 to 5 carbon atoms is an alkoxycarbonyl group derived from one of the above-mentioned alkoxy groups with up to 4 carbon atoms, as for example a methoxycarbonyl, ethoxycarbonyl, propoxycarbonyl, isopropoxycarbonyl, butoxycarbonyl or isobutoxycarbonyl group.

A phenylalkyl radical is for example an 1- or 2- phenylethyl radical, preferably a benzyl radical.

The compounds in accordance with the invention of the general formula I, their tautomers and their pharmacologically-compatible salts with organic and inorganic acids possess valuable pharmacological properties and can accordingly be used as medicaments. More particularly for such a group of substances they have a novel inhibiting action with respect to the ferment xanthine oxidase and have an extraordinarily low toxicity. The new compounds when orally administered to rats bring about a pronounced lowering in the uric acid blood level. The same applies for the 4(1H)-pyrimidinones, described in what follows and their salts with organic and inorganic acids.

The compounds in accordance with the invention of the general formula I and their pharmacologically-compatible salts with inorganic and organic acids can therefore find application as valuable therapeutic substances, preferably for the treatment of gout, and furthermore as an agent for the treatment of coronary insufficiency with an antiarrhythmic action, and as valuable intermediates, as for example for the production of other compounds, more particularly pharmacologically-active ones.

From the compounds in accordance with the invention it is possible to produce 4(1H)-pyrimidinones, for example, as they are described applicant's copending application Ser. No. 393,814 4(1H)-pyrimidinones wherein 4-(1H)-pyrimidinone compounds of the general formula

and their salts with organic or inorganic acids, in which $R^3$ is an organic acid acyl are produced from the compounds in accordance with the invention by heating a compound for the formula I or its tautomers or salts with an organic or inorganic acid and/or treating it with organic or inorganic acids and, if desired, in a compound obtained with a salt forming group converting a free compound into its salt, more particularly a pharmacologically-compatible one or converting a salt obtained into the free compound or into another salt, more particularly a pharmacologically-compatible one. The compounds of the formula I are heated with or without inert organic solvents or mixtures of solvents, preferably to temperatures of 100° to 180° C; or are treated with organic or inorganic acids with or without organic solvents or solvent mixtures while cooling or at raised temperatures, preferably at 0° to 100° C, more particularly 70° to 100° C, and preferably under anhydrous conditions.

Suitable organic solvents are for example benzene, toluene, xylene and o-dichlorobenzene. As organic or inorganic acids it is possible to use for example a hydrogen halide, preferably hydrogen chloride, p-toluenesulfonic acid, acetic acid, sulfuric acid or perchloric acid, use being preferably made of acetic acid. If the ring closing action is carried out in the presence of acids, the acids should be present at least in catalytic quantities. The above-mentioned 4(1H)-pyrimidinones and their pharmacologically-compatible salts with organic or inorganic acids can be used as valuable therapeutic substances, preferably for the treatment of gout, and also as agents for the treatment of coronary insufficiency and with an antiarrhythmic action.

Of the compounds of the formula I compounds of the general formula I*

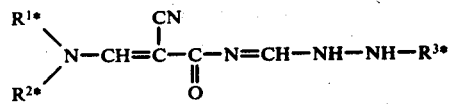

and their tautomers and salts with organic and inorganic acids have a particularly satisfactory effect, in the case of which $R^{1*}$ and $R^{2*}$ are the same or different and denote a straight chained or branch chained alkyl group with 1 to 4, more particularly 1 or 2, carbon atoms or a cyclohexyl radical or $R^{1*}$ and $R^{2*}$ together denote —CH$_2$—CH$_2$—CH$_2$—CH$_2$— or —CH$_2$—CH$_2$—CH$_2$—CH$_2$—CH$_2$—, and more particularly a —CH$_2$—CH$_2$—O—CH$_2$—CH$_2$— or a —CH$_2$—CH$_2$—N(R$^{7*}$)—CH$_2$—CH$_2$—group, and $R^{7*}$ denotes a hydrogen atom, an alkyl radical with 1 or 2 carbon atoms, possibly substituted by a hydroxy group, or furthermore a phenyl radical, possibly substituted by an alkyl- or more particularly alkoxy group with 1 or 2 carbon atoms and $R^{3*}$ denotes a

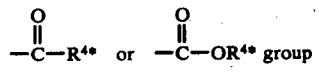

or furthermore a

$R^{4*}$ denotes a branch chained or straight chained alkyl radical with 1 to 14 and more particularly 1 to 7 carbon atoms, in the case of which possibly a methylene group can be replaced by an oxygen atom, or furthermore a phenyl radical, a benzyl radical or a cycloalkyl radical with 3 to 6 carbon atoms, as for example preferably a cyclohexyl radical, in the case of which an alkyl or cycloalkyl radical can possibly be substituted by a salt-forming basic group as for example more especially a —NR$^{5*}$R$^{6*}$group, $R^{5*}$ and $R^{6*}$ are the same or different and denote a hydrogen atom or a branch or straight chained alkyl group with 1 to 4 carbon atoms, more particularly a hydrogen atom or a methyl group, primarily N-methoxycarbonyl-N''-(3-diethylamino-2-cyanoacryloyl) formamidrazone, N-methoxycarbonyl-N''-(3-morpholino-2-cyanoacryloyl) formamidrazone, N-methoxycarbonyl-N''-[3-(4-methylpiperazinyl)-2-cyanoacryloyl]-formamidrazone, N-methoxycarbonyl-N''-(3-[4-(2-hydroxyethyl)-piperazinyl]-2-cyanoacryloyl]-formamidrazone and N-methoxycarbonyl-N''-(3-dimethylamino-2-cyanoacryloyl)-formamidrazone, which in doses of 10 to 100 mg/kg exhibit a pronounced reduction in the uric acid level in the case of oral administration to rats.

The subject matter of the invention furthermore comprises a method for the production of compounds of the general formula I and their tautomers and salts with organic and inorganic acids, characterised in that a. a 4-(1H)-pyrimidinone compound of general formula II

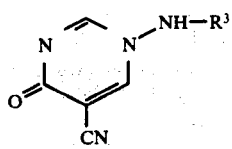  II in which $R^3$ has the above-mentioned meaning is reacted with an amine of general formula III

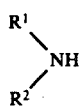  III in which $R^1$ and $R^2$ have the above-mentioned meaning, or b. a compound of general formula IV

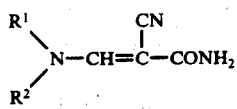  IV in which $R^1$ and $R^2$ have the above-mentioned meanings is reacted with a trialkyl orthoformate [HC(OR)$_3$] or a dialkoxymethyl ester of an aliphatic carboxylic acid [R'COOCH(OR)$_2$] in the presence of an acid anhydride and the reaction product obtained is reacted with a hydrazine derivative of the formula V $$H_2N-NH-R^3 \quad\quad V$$

in which $R^3$ has the above-mentioned meaning, and if desired in the case of a compound obtained in accordance with (a) or (b) a free compound is converted into a salt, more particularly a pharmacologically-compatible salt or a salt obtained is converted into the free compound or into another salt, more particularly a pharmacologically-compatible salt.

In the case of the reaction of a compound of the formula II with a compound of the formula III in accordance with the form (a) of the method the operation is preferably carried out in an inert organic solvent or solvent mixture as for example benzene, toluene, xylene, dioxan, ethyl acetate, chloroform, dimethylformamide, acetonitrile or in alcohols, as for example ethanol or isopropanol and preferably in methanol, while cooling or at a raised temperature, preferably at temperatures between 0° and 100° C and more particularly between 20° and 30° C.

In accordance with the form (b) of the method a compound IV is reacted with an trialkyl orthoformate or a dialkoxymethyl ester of an organic carboxylic acid with or preferably without the presence of an inert organic solvent as for example benzene, toluene, xylene, o-dichlorobenzene, the temperature of the reaction being room temperature or preferably between 50° and 150° C and more particularly between 80° and 120° C or at the boiling point of the solvent. In this respect in the case of the reaction of IV with alkyl orthoformates the operation is preferably carried out in the presence of at least equimolar quantities of anhydride and in the case of the reaction of IV with dialkoxymethyl esters the operation is preferably carried out in the presence of at least catalytic quantities of anhydride, the orthoester or dialkoxymethyl ester preferably being used in excess and more particularly in quantities equal to 2 to 4 times the molar quantity of IV.

The reaction of the reaction product obtained from IV and the alkyl orthoformate or, respectively, dialkoxymethyl ester of an organic carboxylic acid with the hydrazine derivative V is preferably carried out in an inert organic solvent as for example in chloroform, benzene, toluene, xylene, dioxan, dimethylformamide and more particularly ethyl acetate while cooling, at room temperature or preferably at raised temperatures and more particularly between 50° and 150° C or at the boiling temperature of the solvent.

Trialkyl orthoformates [HC(OR)$_3$] are esters in which R denotes an alkyl group with 1 to 7 and preferably 1 to 4, carbon atoms and in particular trimethyl or triethyl orthoformate.

Dialkoxymethyl esters of organic carboxylic acids R'COOCH(OR)$_2$ are such esters, in which R' denotes an organic radical, as for example aryl, aralkyl, cycloalkyl and preferably a hydrogen atom or an alkyl group with 1 to 7, preferably 1 to 4 carbon atoms and R denotes an alkyl group with 1 to 7 and preferably 1 to 4 carbon atoms and in particular the (dimethoxymethyl) acetate or the (diethoxymethyl) acetate.

Acid anhydrides are anhydrides or mixed anhydrides of organic carboxylic acid with preferably 1 to 4 carbon atoms as for example propionic anhydride or butyric anhydride and more particularly acetic anhydride or formic-acetic anhydride. In this respect it can be convenient to add additionally to the anhydride (at least when it is a question of an anhydride which is different to the mixed anhydride containing the formic acid component) at least a catalytic quantity of formic acid, so that the reaction time is reduced.

The reaction product obtained by the reaction of IV with the trialkyl orthoformate or a (dialkoxymethyl) ester of an organic carboxylic acid is found on the basis of NMR-measurements to be a mixture of

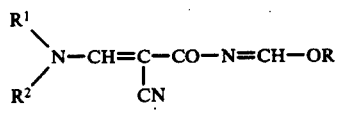  VI and

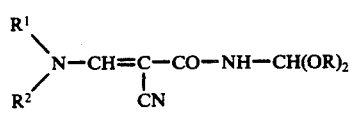  VII or their tautomeric forms, in which R, $R^1$ and $R^2$ have the above-mentioned meanings.

The reaction conditions for the preceding reactions are selected with due regard to all substituents of the reaction partners.

The invention includes those method embodiments which start with a compound, such as a compound of formula VI and/or one of formula VII, isolated (or not)

at some stage or other of the method as an intermediate product and continue with required additional method steps. According to the invention the method may, but need not, be interrupted at any stage; any compound produced while carrying out the method is, alternatively, isolated and then used as a starting material for any ensuing reaction under suitable reaction conditions. The invention further contemplates the use of any starting material and/or intermediate in the form of a reactive derivative, a tautomer or a salt thereof.

Compounds of formula I with salt-forming basic groups, e.g. —$NR^5R^6$, are obtained (depending on reaction conditions) in free-base form or in acid-addition salt form. These several forms are conventionally interconverted.

Compounds of formula I in acid-addition salt form vary in water solubility from those which are readily to those which are sparingly water soluble. The sparingly-soluble salts are particularly suitable for producing retard forms of compounds within the scope of this invention.

Preferred starting materials for methods according to the invention are those which lead to compounds which were previously stated to be particularly valuable.

Starting materials of formula II, their synthesis and their use are disclosed in copending application Ser. No. 394,814, filed on Sept. 4, 1973. The entire disclosure of this copending United States application is incorporated herein by reference. The compounds IV are obtained by reaction, preferably at a reaction temperature of 50° to 80° C, of cyanacetamide with formamide acetals $R^1R^2N$—$CH(OR)_2$, in which R, $R^1$ and $R^2$ have the above-mentioned meanings. The reaction is carried out in an organic solvent, such as an alcohol ROH, or more particularly with in an excess of the formamide acetal. After concentration of the reaction mixture by evaporation in vacuo the compounds IV are obtained and recrystallized. Compounds IV, in which $R^1$ and $R^2$ together denote a 3-oxapentamethylen group, can also be prepared according to Belgian patent specification 727,754.

Dialkoxymethyl esters of an organic carboxylic acid can, for example, be produced in accordance with the method described by J. W. Scheeren and W. Stevens, Rec. 85 [1966] 793.

The compounds of the formula V are known or can be produced in accordance with known methods. Hydrazine derivatives of the formula V, in which case $R^3$ denotes an acyl group can be procuded by reacton of the corresponding chloroformic acid esters with hydrazine hydrate as described by H. Böshagen and J. Ullrich, Chem. Ber. 92 [1959] 1478–80.

4-Phenylsemicarbazide can be obtained from phenylurea and hydrazine hydrate (Houben-Weyl, vol. 8, 167; Organic Synthesis Coll. Vol. I, 2nd Edition, 1948, page 450); 4,4-dimethylsemicarbazide can be produced from chloroformic acid-dimethylamide and hydrazine hydrate, 4-methylsemicarbazide can be produced from methyl isocyanate and hydrazine hydrate (Rec. Trav. Chim. Pays-Bas 62, 5; C. 1944, 541).

Medicaments or pharmaceutical compositions which contain one or more compounds of formula I (in a free form or in the form of a pharmacologically-compatible acid-addition salt) as active substance can, but need not, contain other pharmacologically-active substance. Such medicaments are produced in a conventional manner by combining the active substance with a pharmaceutical vehicle, such as a filler, a diluent, a correcting agent and/or components conventional for medicaments. The medicaments are produced in a solid dosage form as, e.g., tablets or capsules, or in a liquid form as, e.g., solutions or suspensions. The pharmaceutical vehicle can also contain conventional diluent and tablet-forming additions, such as cellulose powder, maize starch, lactose and talcum, as conventional for such purposes.

The production of a pharmaceutical preparation is carried out in a conventional manner, for example by means of conventional mixing, granulating and coating methods. The pharmaceutical preparations contain from approximately 0.1 % to 75 %, preferably from 1 % to approximately 50 %, by weight of the active substance. Administration is enteral, for example oral, or parenteral; individual doses of active substance are between 0.1 and 10, preferably from 0.5 to 5, mg/kg of body weight. For application in human medicine these doses correspond to an individual dose of approximately 10 to 1000, preferably 50 to 500, mg of active substance.

The indicated doses are administered one to four times daily, for example at mealtimes and/or in the evening. The individual dose, the frequency of administration and the duration of treatment are determined by the nature and severity of the illness.

The invention thus relates to medicaments, particularly for treating gout but also for cardiac insufficiency and arrhythmia. The medicaments are characterized by a content of one or more compounds of formula I in a free form or in the form of pharmacologically-compatible salts.

Without further elaboration, one skilled in the art can, using the preceding description, utilize the present invention. The following specific embodiments are merely illustrative and not limitative of the remainder of the disclosure or of the invention described therein in any way whatsoever.

Example of a batch for the production of 75 000 tablets each containing 100 mg of active substance Components:
- 7.500 kg of N-methoxycarboxyl-N''-(2-cyano-3-morpholino-acryloyl)+formamidrazone
- 4.875 kg of maize starch
- 0.225 kg amorphous silicic acid
- 0.300 kg sodium lauryl sulfate
- 0.375 kg polyvinylpyrrolidone
- 1.200 kg pectin
- 0.375 kg talc
- 0.150 kg magnesium stearate
- 15.000 kg The active substance, the maize starch, the amorphous silicic acid and the sodium lauryl sulfate are mixed and sieved. This mixture is moistened with a solution of the polyvinylpyrrolidone in 2.4 l of ethanol and granulated through a sieve with a mesh width of 1.25 mm. The granulate is dried at 40° C and mixed with the pectin, talc and magnesium stearate. This mixture is then pressed on a circular running machine to produce 100 mg tablets with a diameter of 8 mm.

Example of a batch for the production of 200,000 capsules each containing 100 mg of active substance Components:
- 20.000 kg N-acetyl-N''-(2-cyano-3-morpholino-acryloyl)+formamidrazone
- 0.050 kg amorphous silicic acid
- 20.050 kg The active substance in a finely powdered form and the unpressed amorphous silicic acid are well mixed and filled into hard gelatine capsules, size 4.

EXAMPLES

EXAMPLE 1

30 g of methyl N-[5-cyano-4(1H)-oxo-1-pyrimidine]amino-formate and 15.5 g of N-methylpiperazine are stirred in 200 ml of methanol for 2 hours at room temperature. Vacuum filtration is carried out to produce 33.8 g of N-methoxycarbonyl-N''-[3-(4-methyl-piperazinyl)-2-cyano-acryloyl]-methylpiperazinyl)-2-cyanoacryloyl]formamidrazone (74 % of the theoretical amount) of a melting point of 170° C (decomposition).

In a similar manner by the use of the corresponding starting materials the following compounds of formula I ($R^3$= methoxycarbonyl) can be produced:

| $R^1R^2N-$ | Melting point (° C) | Yield (%) |
|---|---|---|
| $H_3C$\N—/$H_3C$ | 184–185 | 63 |
| $H_5C_2$\N—/$H_5C_2$ | 145 (decomposition) | 70 |
| ⌬N— (pyrrolidine) | 193 (decomposition) | 80.5 |
| ⌬N— (piperidine) | 175 (decomposition) | 81 |
| O⌬N— (morpholine) | 185 (decomposition) | 81 |
| phenyl-piperazine with OCH₃ | 182 (decomposition) | 75 |
| HOCH₂CH₂—N⌬N— | 164 (decomposition) | 80 |
| ⌬H—NH— (cyclohexylamine) | 152–153 | 56.4 |

EXAMPLE 2

5 g of 3-morpholino-2-cyanoacrylamide, 8.8 g of triethyl orthoformate and 8.45 g of acetic anhydride are heated for 10 hours at 100° C and then evaporated in a rotary evaporator. The residue, a yellow oil, $R_f$ = 0.33 (thin layer on silica gel neutral, chloroform/acetonontrile = 6/4) is mixed with 30 ml of ethyl acetate. Separation from the undissolved material is carried out by vacuum, 2.5 g of acetylhydrazine is added to the filtrate and stirring is carried out for 30 minutes at room temperature. 5.5 g of N-acetyl-N''-(3-morpholino-2-cyanoacryloyl) formamidrazone (74 % of the theoretical amount) with a melting point of 243° C are obtained.

EXAMPLE 3

2 g of 3-morpholino-2-cyanoacrylamide, 2 g of diethoxymethyl acetate and 5.6 ml of acetic anhydride are heated for 1 hour at 100° C. The reaction mixture is reduced in volume on a rotary evaporator and mixed with 20 ml of ethyl acetate and 1 g of acetylhydrazine. Stirring is carried out for 10 minutes at room temperature followed by vacuum filtration to produce 1.8 g of N-acetyl-N''-(3-morpholino-2-cyanoacryloyl)-formamidrazone (62.5 % of the theoretical amount) with a melting point of 243° C.

EXAMPLE 4

5 g of 3-morpholino-2-cyano-acrylamide, 12.3 g of triethyl orthoformate, 8.45 g of acetic anhydride and 1.3 g of formic acid are heated for 1 hour at 100° C. Evaporation is carried out in a rotary evaporator, the residue is mixed with 30 ml of ethyl acetate and separation from undissolved material is carried out by suction. The filtrate is stirred up with 2.5 g of acetylhydrazine for 30 minutes at room temperature. 5.1 g of N-acetyl-N''-(3-morpholino-2-cyanoacryloyl) formamidrazone are obtained (70 % of the theoretical amount) with a melting point of 243° C.

Using formylhydrazine or propionylhydrazine instead of acetylhydrazine, in an analogous manner there are obtained N-formyl-N''-(3-morpholino-2-cyanoacryloyl) formamidrazone (61.5 % of the theoretical amount) with a melting point of 177°–179° C, or N-propionyl-N''-(3-morpholino-2-cyanoacryloyl)formamidrazone (56.8 % of the theoretical amount) with a melting point of 183°–185° C.

What is claimed is:

1. A therapeutically-active and pharmacologically-acceptable xanthine-oxidase-inhibiting compound selected from the group consisting of (a) an N-acyl-N'''-(3-amino-2-cyanoacryloyl)-formamidrazone, (b) a tautomer of (a), and (c) a salt of (a) with an organic or inorganic acid, the acyl of which is hydrocarbylacyl of a carboxylic or carbonic acid having from 1 to 14 carbon atoms, any ring of which has at most 6 ring carbon atoms and any unsaturation of which is aromatic unsaturation.

2. A compound of the formula

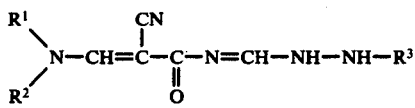

wherein
 $R^1$ is a member selected from the group consisting of straight- or branch-chained alkyl with from 1 to 7 carbon atoms and cycloalkyl with from 3 to 6 carbon atoms;
 $R^2$ is —H or one of the meanings of $R^1$; or
 $R^1$ and $R^2$ together denote (a) pentamethylene or (b) pentamethylene in which at least one methylene is replaced by a member selected from the group consisting of —O—, —S— and —$NR^7$—;
 $R^3$ is a member selected from the group consisting of CO—$R^4$, —CO—$OR^4$ and —CO—$N(R^5)R^6$
 $R^4$ is an $R^5(R^6)N$-substituted or unsubstituted member selected from the group consisting of straight- or branch-chained alkyl with from 1 to 14 carbon atoms, a methylene (other than a methylene) group of which is optionally replaced by an oxygen atom;

cycloalkyl with from 3 to 6 carbon atoms; phenyl; phenyl substituted by at least one member selected from the group consisting of straight- or branch-chained alkyl, alkoxy or alkylmercapto having from 1 to 7 carbon atoms, alkoxycarbonyl with from 2 to 5 carbon atoms, halo, trifluoromethyl, nitro and cyano; phenylalkyl, the alkyl of which has from 1 to 6 carbon atoms and the phenyl of which is optionally substituted by at least one member selected from the group consisting of straight- or branch-chained alkyl, alkoxy or alkylmercapto having from 1 to 7 carbon atoms, alkoxycarbonyl with from 2 to 5 carbon atoms, halo, trifluoromethyl, nitro and cyano; or a $C_{3-6}$—cycloalkyl substituted by —N($R^5$)$R^6$;

each of $R^5$ and $R^6$ is, independently, a member selected from the group consisting of -H; straight- or branch-chained alkyl with from 1 to 7 carbon atoms, a methylene group of which is optionally replaced by an oxygen atom; and cycloalkyl with from 3 to 6 carbon atoms; or $R^5$ and $R^6$ together denote alkylene with from 2 to 5 carbon atoms or such alkylene in which at least one methylene group is replaced by —O—, —S— or —$NR^7$—;

$R^7$ is a member selected from the group consisting of —H; hydroxy-substituted or unsubstituted straight- or branch-chained alkyl with from 1 to 7 carbon atoms; and phenyl optionally substituted by straight- or branch-chained alkyl or alkoxy with from 1 to 7 carbon atoms, halo or trifluoromethyl.

3. A compound according to claim 2 wherein each of $R^1$ and $R^2$ has from 1 to 4 carbon atoms when it is alkyl, any alkyl substituent of substituted phenyl in the definition of $R^4$ has at most 4 carbon atoms, any alkyl of phenylalkyl in the definition of $R^4$ has at most 2 carbon atoms, each of $R^5$ and $R^6$ has from 1 to 4 carbon atoms when it is alkyl, and $R^7$ has from 1 to 5 carbon atoms when it is hydroxy-substituted or unsubstituted alkyl.

4. A compound according to claim 2 wherein $R^1$ is a member selected from the group consisting of straight- or branch-chained alkyl with from 1 to 4 carbon atoms and cyclohexyl or, together with $R^2$, —CH$_2$—CH$_2$—CH$_2$—CH$_2$—, —CH$_2$—CH$_2$—CH$_2$—CH$_2$—CH$_2$—, —CH$_2$—CH$_2$—O—CH$_2$—CH$_2$— or—CH$_2$—CH$_2$—N($R^7$)—CH$_2$—CH$_2$—;

$R^2$ is a member selected from the group consisting of straight- or branch-chained alkyl with from 1 to 4 carbon atoms and cyclohexyl or, together with $R^1$, —CH$_2$—CH$_2$—CH$_2$—CH$_2$—, —CH$_2$—CH$_2$—CH$_2$—CH$_2$—CH$_2$—, —CH$_2$—CH$_2$—O—CH$_2$—CH$_2$— or —CH$_2$—CH$_2$—N($R^7$)—CH$_2$—CH$_2$—;

$R^4$ is substituted or unsubstituted straight- or branch-chained alkyl with from 1 to 14 carbon atoms and optionally interrupted by an oxygen atom; phenyl; benzyl; substituted or unsubstituted cycloalkyl with from 3 to 6 carbon atoms; any substituent of substituted alkyl being — N($R^5$)$R^6$ and any substituent of cycloalkyl being —N($R^5$)$R^6$ or alkyl;

each of $R^5$ and $R^6$ is, independently, a member selected from the group consisting of —H and straight- or branch-chained alkyl having from 1 to 4 carbon atoms; and $R^7$ is a member selected from the group consisting of —H, unsubstituted or hydroxy-substituted alkyl with 1 or 2 carbon atoms, phenyl, $C_{1-2}$-alkylphenyl and $C_{1-2}$-alkoxyphenyl.

5. A compound according to claim 4 wherein each of $R^1$ and $R^2$ has 1 or 2 carbon atoms when it is alkyl, $R^4$ has from 1 to 7 carbon atoms when it is alkyl or alkyl optionally interrupted by an oxygen atom, and each or $R^5$ and $R^6$ is, independently, —H or methyl.

6. A compound according to claim 4 wherein $R^1$ is a member selected from the group consisting of methyl, ethyl and cyclohexyl or, together with $R^2$, —CH$_2$—CH$_2$—O—CH$_2$—CH$_2$— or —CH$_2$—CH$_2$—N($R^5$)—CH$_2$—CH$_2$—;

$R^2$ is a member selected from the group consisting of methyl, ethyl and cyclohexyl or, together with $R^1$, —CH$_2$—CH$_2$—O—CH$_2$—CH$_2$— or —CH$_2$—CH$_2$—N($R^7$)—CH$_2$—CH$_2$—;

$R^4$ has the meaning accorded it in claim 31; and $R^7$ is a member selected from the group consisting of -H, methyl, ethyl and 2-hydroxyethyl.

7. A compound according to claim 6 wherein $R^4$ has from 1 to 7 carbon atoms when it is alkyl or alkyl with a methylene group replaced by an oxygen atom; cycloalkyl is cyclohexyl; and each of $R^5$ and $R^6$ is, independently, —H or methyl.

8. The compound according to claim 2, which is N-methoxycarbonyl-N''-(3-diethylamino-2-cyanoacryloyl) formamidrazone.

9. The compound according to claim 2, which is N-methoxycarbonyl-N''-(3-morpholino-2-cyanoacryloyl) formamidrazone.

10. The compound according to claim 2, which is N-methoxycarbonyl-N''-[3-(4-methylpiperazinyl)-2-cyanoacryloyl]-formamidrazone.

11. The compound according to claim 2, which is N-methoxycarbonyl-N''-(3-[4-(2-hydroxy-ethyl) piperazinyl)-2-cyanoacryloyl] formamidrazone.

12. The compound according to claim 2, which is N-methoxycarbonyl-N''-(3-dimethylamino-2-cyanoacryloyl)-formamidrazone.

13. A compound according to claim 2: wherein $$R^3 \text{ is } -\overset{\overset{\displaystyle O}{\|}}{C}-R^4;$$

and $R^4$ is straight- or branch-chain alkyl with from 1 to 14 carbon atoms and optionally interrupted by an oxygen atom, or cycloalkyl with from 3 to 6 carbon atoms.

14. A compound according to claim 13 wherein $R^4$ is straight- or branch-chain alkyl with from 1 to 14 carbon atoms or cycloalkyl with from 3 to 6 carbon atoms.

15. A compound according to claim 2: wherein $R^4$ is hydrocarbyl acyl having from 1 to 14 carbon atoms, any ring of which has at most 6 carbon atoms and any unsaturation of which is aromatic unsaturation.

16. A compound according to claim 2: wherein $R^4$ is substituted or unsubstituted alkyl, a methylene group of which is optionally replaced by an oxygen atom.

17. A compound according to claim 16 wherein $R^4$ is unsubstituted alkyl, a methylene group of which is optionally replaced by an oxygen atom.

18. A compound according to claim 2 wherein $$R^3 \text{ is } -\overset{\overset{\displaystyle O}{\|}}{C}-R^4$$

and $R^4$ is a straight- or branched-chain alkyl with from 1 to 14 carbon atoms or cycloalkyl with from 3 to 6 carbon atoms.

19. The compound according to claim 2 which is N-acetyl-N"-(3-morpholino-2-cyanoacryloyl)formamidrazone.

20. A dosage-form medicament composition containing, as a pharmacologically-active component thereof, an effective concentration of at least one compound according to claim 2.

21. A dosage-form medicament composition containing, as a pharmacologically-active component thereof, an effective concentration of at least one compound according to claim 3.

22. A dosage-form medicament composition containing, as a pharmacologically-active component thereof, an effective concentration of at least one compound according to claim 5.

23. A dosage-form medicament composition containing, as a pharmacologically-active component thereof, an effective concentration of at least one compound according to claim 7.

24. A pharmaceutically-acceptable composition which contains a total of from about 0.1 percent to about 75 percent by weight of at least one pharmacologically-active compound according to claim 2.

25. A composition according to claim 24, which contains a total of from 1 to 50 percent by weight of the pharmacologically-active compound.

26. A method which comprises administering an effective amount of a medicament composition according to claim 24 to a subject afflicted with gout.

27. A therapeutically-active and pharmacologically-acceptable xanthine-oxidase-inhibiting compound selected from the group consisting of (a) an N-acyl-N"-(3-amino-2-cyanoacryloyl)formamidrazone according to claim 2, (b) a tautomer of (a), and (c) a salt of (a) with an organic or inorganic acid.

* * * * *